(12) United States Patent
Fenyvesi et al.

(10) Patent No.: US 8,207,372 B2
(45) Date of Patent: Jun. 26, 2012

(54) PROCESS FOR THE PRODUCTION OF ACRYLIC AND METHACRYLIC ESTERS OF POLY(TRIMETHYLENE ETHER) GLYCOL

(75) Inventors: Gyorgyi Fenyvesi, Wilmington, DE (US); Raja Hari Poladi, Bear, DE (US); Hari Babu Sunkara, Hockessin, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 295 days.

(21) Appl. No.: 12/607,157

(22) Filed: Oct. 28, 2009

(65) Prior Publication Data

US 2010/0160672 A1 Jun. 24, 2010

Related U.S. Application Data

(60) Provisional application No. 61/140,238, filed on Dec. 23, 2008.

(51) Int. Cl.
*C07C 69/52* (2006.01)
(52) U.S. Cl. ......... 560/224; 560/205; 526/319; 526/320
(58) Field of Classification Search ............... 560/205, 560/224, 319, 320; 526/319, 320
See application file for complete search history.

(56) References Cited

U.S. PATENT DOCUMENTS

| 2,892,820 | A | * | 6/1959 | Stewart et al. | 526/320 |
|---|---|---|---|---|---|
| 4,038,264 | A | * | 7/1977 | Rostoker et al. | 526/286 |
| 5,364,987 | A | | 11/1994 | Haas et al. | |
| 5,371,280 | A | * | 12/1994 | Haramaki et al. | 562/26 |
| 5,633,362 | A | | 5/1997 | Nagarajan et al. | |
| 5,686,276 | A | | 11/1997 | Laffend et al. | |
| 5,821,092 | A | | 10/1998 | Nagarajan et al. | |
| 6,720,459 | B2 | | 4/2004 | Sunkara et al. | |
| 6,977,291 | B2 | | 12/2005 | Sunkara et al. | |
| 7,038,092 | B2 | | 5/2006 | Sunkara et al. | |
| 7,323,539 | B2 | | 1/2008 | Sunkara et al. | |
| 2002/0007043 | A1 | * | 1/2002 | Sunkara et al. | 528/396 |
| 2002/0188093 | A1 | | 12/2002 | Kroner et al. | |
| 2004/0030095 | A1 | | 2/2004 | Sunkara et al. | |
| 2004/0225107 | A1 | | 11/2004 | Sunkara et al. | |
| 2005/0089666 | A1 | | 4/2005 | Baldwin | |

FOREIGN PATENT DOCUMENTS

| EP | 1260535 B1 | 11/2002 |
|---|---|---|
| WO | 2005005514 A1 | 1/2005 |
| WO | 2008057462 A1 | 5/2008 |

OTHER PUBLICATIONS

Robert V. Hoffman's Organic Chemistry: An Intermediate Text, 2nd edition, published online on Jan. 28, 2005, by John Wiley & Sons, Inc. at http://onlinelibrary.wiley.com/doi/10.1002/0471648736.fmatter/pdf (p. 189).*
Kirk-Othmer Encyclopedia of Chemical Technology, published online on Dec. 19, 2003 by Wiley Online Library at http://onlinelibrary.wiley.com/doi/10.1002/0471238961.05192005200121.a01.pub2/pdf (p. 499).*
See Structure Search (Sep. 14, 2011).*
International Search Report and Written Opinion of the International Searching Authorized, PCT International Application PCT/US2009/062287, Jun. 1, 2010.
Priola, A. et al., Polymer 34 (17) pp. 3653-3657 (1993).
Priola, A. et al., Polymer 37 (12) pp. 2565-2571 (1996).
Priola, A. et al., J. Applied Polymer Sci 65, pp. 491-497 (1997).
Characterization of Environmental Particles, J. Buffle et al., Editors, 1 of vol. I of the IUPAC Environmental Analytical Chemistry Series, Lewis Publishers, Inc., pp. 3-74, (1992). (Book, Not Included).
D. Weber, 13C-Pattern of Natural Glycerol: Origin and Practical Importance, J. Agric. Food Chem., 1997, vol. 45, pp. 2042-2046.
Y-P. Hsieh, Division S-3-Soil Microbiology and Chemistry: Pool Size Andmean Age of Stable Soil Organic Carbon in Cropland, Soil Sci. Soc. Am. J., 1992, vol. 56, pp. 460-464.

* cited by examiner

*Primary Examiner* — David W Wu
*Assistant Examiner* — Vu A Nguyen

(57) ABSTRACT

Processes are provided for producing novel (meth)acrylic esters of poly(trimethylene ether) glycol. The processes include reacting poly(trimethylene ether) glycol with (meth) acrylic acid or equivalents thereof.

7 Claims, No Drawings

PROCESS FOR THE PRODUCTION OF ACRYLIC AND METHACRYLIC ESTERS OF POLY(TRIMETHYLENE ETHER) GLYCOL

FIELD OF THE INVENTION

This invention relates to processes for the production of acrylic and methacrylic acid esters (monoesters and/or diesters) of polytrimethylene ether glycol.

BACKGROUND

Acrylate polymers find use in a number of coatings and radiation curable applications. Most of the acrylates currently in use are those derived from polyether glycols, including poly(ethylene) glycol diacrylate, poly(1,2-propylene) glycol diacrylate and poly(tetramethylene) glycol diacrylate. Acrylate polymers are disclosed in, for example, A. Priola, et al., Polymer 33 (17), 3653, 1993; A. Priola, et al., Polymer 37 (12), 2565, 1996; and A. Priola, et al., J. Appl. Polym. Sci 65 491-497, 1997.

However, some known acrylate polymers can have lower flexibility than needed for certain applications, as well as degradation during production. A need remains for acrylate polymers having desired physical properties and reduced degradation during production.

SUMMARY OF THE INVENTION

One aspect of the present invention is a process for making a (meth)acrylic acid ester of a polytrimethylene ether glycol comprising:
a) polycondensation of hydroxyl groups-containing monomers predominantly comprising 1,3-propanediol obtained biochemically from a renewable source in the presence of acid catalyst at temperatures between 100 to 250° C. to form a poly(trimethylene ether) glycol
b) esterifying the obtained poly(trimethylene ether) glycol with an acrylic compound in the presence of a polymerization inhibitor(s) and optionally a solvent at temperatures between 25 to 250° C.

Another aspect of the present invention is a process for making a a(meth)acrylic acid ester of a polytrimethylene ether glycol comprising: reacting poly(trimethylene ether) glycol having a number average molecular weight from 134 to 5000 with (meth)acrylic acid in the presence of an esterification catalyst, a polymerization inhibitor and optionally a solvent at temperatures between 25 to 250° C.

A further aspect of the present invention is a process for making a (meth)acrylic acid ester of a polytrimethylene ether glycol comprising: reacting poly(trimethylene ether) glycol with (meth)acrylic acid halide in the presence of an organic base or a catalyst at temperatures between 5 to 150° C.

DETAILED DESCRIPTION

The present invention provides novel (meth)acrylic esters of poly(trimethylene ether) glycol. The invention also provides processes for producing the novel (meth)acrylic esters of poly(trimethylene ether) glycol by reacting poly(trimethylene ether) glycol with (meth)acrylic acid or its equivalent. Monocarboxylic acid equivalents include, for example, esters of monocarboxylic acids, and ester-forming derivatives such as acid halides (e.g., acid chlorides) and anhydrides In some embodiments, the poly(trimethylene ether) glycol (meth)acrylates are based on renewably-sourced (biosourced) 1,3-propanediol and polytrimethylene ether glycols.

In one embodiment, the (meth)acrylic ester of poly(trimethylene ether) glycol is produced by first polycondensing 1,3-propanediol reactant in the presence of a catalyst (preferably a mineral acid catalyst) and then esterifying the condensed product with (meth)acrylic acid in the presence of a polymerization inhibitor(s) while removing the byproduct (water) formed both in condensation and esterification reactions simultaneously.

In other embodiment, the (meth)acrylic ester of poly(trimethylene ether) glycol is produced by reacting poly(trimethylene ether) glycol having a number average molecular weight from 134 to 5000 with (meth)acrylic acid in the presence of an esterification catalyst and a polymerization inhibitor while removing the byproduct (water) formed during esterfication simultaneously.

In another embodiment, the (meth)acrylic ester of poly (trimethylene ether) glycol is produced by reacting poly(trimethylene ether) glycol with (meth)acrylic acid chloride in the presence of an organic base while the byproduct (water) formed during esterification reaction. At least one polymerization inhibitor and at least one antioxidant are added to the resulting product.

The products obtained from the above processes comprise mixture of mono and/or diesters of poly(trimethylene ether) glycol and 1,3-propanediol, un-reacted starting materials and catalyst residues. The compositions can be used as such in end use applications or if desired the products can be further purified to remove catalyst residues and un-reacted starting materials by well known separation processes.

Preferably, the 1,3-propanediol and poly(trimethylene ether) glycol used in the above processes are derived from renewable sourced raw materials and therefore the acrylic ester of poly(trimethylene ether) glycols of the present invention have bio content of minimum 20 wt %. The compositions of the present invention thus have a reduced environmental impact.

Unless otherwise defined, all technical and scientific terms used herein have the same meaning as commonly understood by one of ordinary skill in the art to which this invention belongs. In case of conflict, the present specification, including definitions, will control.

Unless stated otherwise, all percentages, parts, ratios, etc., are by weight.

When an amount, concentration, or other value or parameter is given as either a range, preferred range or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Use of "a" or "an" are employed to describe elements and components of the invention. This is done merely for convenience and to give a general sense of the invention. This description should be read to include one or at least one and the singular also includes the plural unless stated otherwise.

The materials, methods, and examples herein are illustrative only and, except as specifically stated, are not intended to be limiting. Although methods and materials similar or equivalent to those described herein can be used in the practice or testing of the present invention, suitable methods and materials are described herein.

The term "(meth)acrylic" may be used herein as shorthand for "acrylic and methacrylic", when referring to acids or esters. Unless otherwise specified, the term, when used, is intended to encompass both "acrylic" and "methacrylic".

The present invention provides (meth)acrylic ester of poly(trimethylene ether) glycol compositions comprising an ester (a monoester, a diester or mixtures thereof) of a polytrimethylene ether glycol and at least one polymerization inhibitor, and processes of producing such compositions.

The (meth)acrylic esters of poly(trimethylene ether) glycol comprise one or more compounds of the formula (I):

$$CH_2=CR_1-C(O)-O-Q-OR_2 \quad (I)$$

wherein Q represents the residue of a poly(trimethylene ether) glycol after abstraction of the hydroxyl groups, $R_1$ is H or $CH_3$, and each of $R_2$ is H or $CH_2=CR_1-C(O)$.

The (meth)acrylic esters of polytrimethylene ether glycol can be produced by various methods using either 1,3-propanediol or poly(trimethylene ether) glycol as a feedstock.

Poly(trimethylene ether) Glycol (PO3G)

PO3G, as used herein, is a polymeric ether glycol in which at least 50% of the repeating units are trimethylene ether units. More preferably from about 75% to 100%, still more preferably from about 90% to 100%, and even more preferably from about 99% to 100%, of the repeating units are trimethylene ether units.

PO3G is preferably prepared by polycondensation of monomers comprising 1,3-propanediol, thus resulting in polymers or copolymers containing —$(CH_2CH_2CH_2O)$— linkage (e.g, trimethylene ether repeating units). As indicated above, at least 50% of the repeating units are trimethylene ether units.

In addition to the trimethylene ether units, lesser amounts of other units, such as other polyalkylene ether repeating units, may be present. In the context of this disclosure, the term "polytrimethylene ether glycol" encompasses PO3G made from essentially pure 1,3-propanediol, as well as those oligomers and polymers (including those described below) containing up to about 50% by weight of comonomers.

The 1,3-propanediol employed for preparing the PO3G may be obtained by any of the various well known chemical routes or by biochemical transformation routes. Preferred routes are described in, for example, U.S. Pat. No. 5,364,987, and U.S. Pat. No. 5,633,362.

Preferably, the 1,3-propanediol is obtained biochemically from a renewable source ("biologically-derived" 1,3-propanediol).

A particularly preferred source of 1,3-propanediol is via a fermentation process using a renewable biological source. As an illustrative example of a starting material from a renewable source, biochemical routes to 1,3-propanediol (PDO) have been described that utilize feedstocks produced from biological and renewable resources such as corn feed stock. For example, bacterial strains able to convert glycerol into 1,3-propanediol are found in the species *Klebsiella, Citrobacter, Clostridium*, and *Lactobacillus*. The technique is disclosed in several publications, including U.S. Pat. No. 5,633,362, U.S. Pat. No. 5,686,276 and U.S. Pat. No. 5,821,092. U.S. Pat. No. 5,821,092 discloses, inter alia, a process for the biological production of 1,3-propanediol from glycerol using recombinant organisms. The process incorporates *E. coli* bacteria, transformed with a heterologous pdu diol dehydratase gene, having specificity for 1,2-propanediol. The transformed *E. coli* is grown in the presence of glycerol as a carbon source and 1,3-propanediol is isolated from the growth media. Since both bacteria and yeasts can convert glucose (e.g., corn sugar) or other carbohydrates to glycerol, the processes disclosed in these publications provide a rapid, inexpensive and environmentally responsible source of 1,3-propanediol monomer.

The renewably sourced (also known as biologically-derived) 1,3-propanediol, such as produced by the processes described and referenced above, contains carbon from the atmospheric carbon dioxide incorporated by plants, which compose the feedstock for the production of the 1,3-propanediol. In this way, the biologically-derived 1,3-propanediol preferred for use in the context of the present invention contains only renewable carbon, and not fossil fuel-based or petroleum-based carbon. The PO3G and elastomers based thereon utilizing the biologically-derived 1,3-propanediol, therefore, have less impact on the environment as the 1,3-propanediol used in the compositions does not deplete diminishing fossil fuels and, upon degradation, releases carbon back to the atmosphere for use by plants once again. Thus, the compositions of the present invention can be characterized as more natural and having less environmental impact than similar compositions comprising petroleum based glycols.

The renewably sourced (also known as biologically-derived) 1,3-propanediol, PO3G and PO3G acrylate esters, may be distinguished from similar compounds produced from a petrochemical source or from fossil fuel carbon by dual carbon-isotopic finger printing. This method usefully distinguishes chemically-identical materials, and apportions carbon in the copolymer by source (and possibly year) of growth of the biospheric (plant) component. The isotopes, $^{14}C$ and $^{13}C$, bring complementary information to this problem. The radiocarbon dating isotope ($^{14}C$), with its nuclear half life of 5730 years, clearly allows one to apportion specimen carbon between fossil ("dead") and biospheric ("alive") feedstocks (Currie, L. A. "Source Apportionment of Atmospheric Particles," *Characterization of Environmental Particles*, J. Buffle and H. P. van Leeuwen, Eds., 1 of Vol. I of the IUPAC Environmental Analytical Chemistry Series (Lewis Publishers, Inc) (1992) 3-74). The basic assumption in radiocarbon dating is that the constancy of $^{14}C$ concentration in the atmosphere leads to the constancy of $^{14}C$ in living organisms. When dealing with an isolated sample, the age of a sample can be deduced approximately by the relationship:

$$t=(-5730/0.693)\ln(A/A_0)$$

wherein t=age, 5730 years is the half-life of radiocarbon, and A and $A_0$ are the specific $^{14}C$ activity of the sample and of the modern standard, respectively (Hsieh, Y., *Soil Sci. Soc. Am J.*, 56, 460, (1992)). However, because of atmospheric nuclear testing since 1950 and the burning of fossil fuel since 1850, $^{14}C$ has acquired a second, geochemical time characteristic. Its concentration in atmospheric $CO_2$, and hence in the living biosphere, approximately doubled at the peak of nuclear testing, in the mid-1960s. It has since been gradually returning to the steady-state cosmogenic (atmospheric) baseline isotope rate ($^{14}C/^{12}C$) of ca. $1.2 \times 10^{-12}$, with an approximate relaxation "half-life" of 7-10 years. (This latter half-life must not be taken literally; rather, one must use the detailed atmospheric nuclear input/decay function to trace the variation of atmospheric and biospheric $^{14}C$ since the onset of the nuclear age.) It is this latter biospheric $^{14}C$ time characteristic that holds out the promise of annual dating of recent biospheric carbon. $^{14}C$ can be measured by accelerator mass spectrometry (AMS), with results given in units of "fraction of modern carbon" ($f_M$). $f_M$ is defined by National Institute of Standards and Technology (NIST) Standard Reference Materials (SRMs) 4990B and 4990C, known as oxalic acids standards HOxI and HOxII, respectively. The fundamental definition relates to 0.95 times the $^{14}C/^{12}C$ isotope ratio HOxI (referenced to AD 1950). This is roughly equivalent to decay-corrected pre-Industrial Revolution wood. For the current living biosphere (plant material), $f_m \approx 1.1$.

The stable carbon isotope ratio ($^{13}C/^{12}C$) provides a complementary route to source discrimination and apportionment. The $^{13}C/^{12}C$ ratio in a given renewably sourced material is a consequence of the $^{13}C/^{12}C$ ratio in atmospheric carbon dioxide at the time the carbon dioxide is fixed and also reflects the precise metabolic pathway. Regional variations also occur. Petroleum, $C_3$ plants (the broadleaf), $C_4$ plants (the grasses), and marine carbonates all show significant differences in $^{13}C/^{12}C$ and the corresponding $\delta\ ^{13}C$ values. Furthermore, lipid matter of $C_3$ and $C_4$ plants analyze differently than materials derived from the carbohydrate components of the same plants as a consequence of the metabolic pathway. Within the precision of measurement, $^{13}C$ shows large variations due to isotopic fractionation effects, the most significant of which for the instant invention is the photosynthetic mechanism. The major cause of differences in the carbon isotope ratio in plants is closely associated with differences in the pathway of photosynthetic carbon metabolism in the plants, particularly the reaction occurring during the primary carboxylation, i.e., the initial fixation of atmospheric $CO_2$. Two large classes of vegetation are those that incorporate the "$C_3$" (or Calvin-Benson) photosynthetic cycle and those that incorporate the "$C_4$" (or Hatch-Slack) photosynthetic cycle. $C_3$ plants, such as hardwoods and conifers, are dominant in the temperate climate zones. In $C_3$ plants, the primary $CO_2$ fixation or carboxylation reaction involves the enzyme ribulose-1,5-diphosphate carboxylase and the first stable product is a 3-carbon compound. $C_4$ plants, on the other hand, include such plants as tropical grasses, corn and sugar cane. In $C_4$ plants, an additional carboxylation reaction involving another enzyme, phosphenol-pyruvate carboxylase, is the primary carboxylation reaction. The first stable carbon compound is a 4-carbon acid, which is subsequently decarboxylated. The $CO_2$ thus released is refixed by the $C_3$ cycle.

Both $C_4$ and $C_3$ plants exhibit a range of $^{13}C/^{12}C$ isotopic ratios, but typical values are ca. −10 to −14 per mil ($C_4$) and −21 to −26 per mil ($C_3$) (Weber et al., *J. Agric. Food Chem.*, 45, 2042 (1997)). Coal and petroleum fall generally in this latter range. The $^{13}C$ measurement scale was originally defined by a zero set by pee dee belemnite (PDB) limestone, where values are given in parts per thousand deviations from this material. The "$\delta^{13}C$" values are in parts per thousand (per mil), abbreviated ‰, and are calculated as follows:

$$\delta^{13}C \equiv \frac{(^{13}C/^{12}C)\text{sample} - (^{13}C/^{12}C)\text{standard}}{(^{13}C/^{12}C)\text{standard}} \times 1000\text{‰}$$

Since the PDB reference material (RM) has been exhausted, a series of alternative RMs have been developed in cooperation with the IAEA, USGS, NIST, and other selected international isotope laboratories. Notations for the per mil deviations from PDB is $\delta^{13}C$. Measurements are made on $CO_2$ by high precision stable ratio mass spectrometry (IRMS) on molecular ions of masses 44, 45 and 46.

Renewably sourced (also known as biologically-derived) 1,3-propanediol, and compositions comprising renewably sourced (biologically-derived) 1,3-propanediol, therefore, may be completely distinguished from their petrochemical derived counterparts on the basis of $^{14}C$ ($f_M$) and dual carbon-isotopic fingerprinting, indicating new compositions of matter. The ability to distinguish these products is beneficial in tracking these materials in commerce. For example, products comprising both "new" and "old" carbon isotope profiles may be distinguished from products made only of "old" materials. Hence, the instant materials may be followed in commerce on the basis of their unique profile and for the purposes of defining competition, for determining shelf life, and especially for assessing environmental impact.

Preferably the 1,3-propanediol used as the reactant or as a component of the reactant has a purity of greater than about 99%, and more preferably greater than about 99.9%, by weight as determined by gas chromatographic analysis. Particularly preferred are the purified 1,3-propanediols as disclosed in U.S. Pat. No. 7,038,092, as well as PO3G made as disclosed in US20050020805A1.

The purified 1,3-propanediol preferably has the following characteristics:

(1) an ultraviolet absorption at 220 nm of less than about 0.200, and at 250 nm of less than about 0.075, and at 275 nm of less than about 0.075; and/or (2) a composition having L*a*b*"b*" color value of less than about 0.15 (ASTM D6290), and an absorbance at 270 nm of less than about 0.075; and/or (3) a peroxide composition of less than about 10 ppm; and/or (4) a concentration of total organic impurities (organic compounds other than 1,3-propanediol) of less than about 400 ppm, more preferably less than about 300 ppm, and still more preferably less than about 150 ppm, as measured by gas chromatography.

The starting material for making PO3G will depend on the desired PO3G, availability of starting materials, catalysts, equipment, etc., and comprises "1,3-propanediol reactant." By "1,3-propanediol reactant" is meant 1,3-propanediol, and oligomers and prepolymers of 1,3-propanediol preferably having a degree of polymerization of 2 to 9, and mixtures thereof. In some instances, it may be desirable to use up to 10% or more of low molecular weight oligomers where they are available. Thus, preferably the starting material comprises 1,3-propanediol and the dimer and trimer thereof. A particularly preferred starting material is comprised of about 90% by weight or more 1,3-propanediol, and more preferably 99% by weight or more 1,3-propanediol, based on the weight of the 1,3-propanediol reactant.

PO3G can be made via a number of processes known in the art, such as disclosed in U.S. Pat. No. 6,977,291 and U.S. Pat. No. 6,720,459. A preferred process is as set forth in US20050020805A1.

As indicated above, PO3G may contain lesser amounts of other polyalkylene ether repeating units in addition to the trimethylene ether units. The monomers for use in preparing polytrimethylene ether glycol can, therefore, contain up to 50% by weight (preferably about 20 wt % or less, more preferably about 10 wt % or less, and still more preferably about 2 wt % or less), of comonomer polyols in addition to the 1,3-propanediol reactant. Comonomer polyols that are suitable for use in the process include aliphatic diols, for example, ethylene glycol, 1,6-hexanediol, 1,7-heptanediol, 1,8-octanediol, 1,9-nonanediol, 1,10-decanediol, 1,12-dodecanediol, 3,3,4,4,5,5-hexafluoro-1,5-pentanediol, 2,2,3,3,4, 4,5,5-octafluoro-1,6-hexanediol, and 3,3,4,4,5,5,6,6,7,7,8,8, 9,9,10,10-hexadecafluoro-1,12-dodecanediol; cycloaliphatic diols, for example, 1,4-cyclohexanediol, 1,4-cyclohexanedimethanol and isosorbide; and polyhydroxy compounds, for example, glycerol, trimethylolpropane, and pentaerythritol. A preferred group of comonomer diols is selected from the group consisting of ethylene glycol, 2-methyl-1,3-propanediol, 2,2-dimethyl-1,3-propanediol, 2,2-diethyl-1,3-propanediol, 2-ethyl-2-(hydroxymethyl)-1,3-propanediol, $C_6$-$C_{10}$ diols (such as 1,6-hexanediol, 1,8-octanediol and 1,10-decanediol) and isosorbide, and mixtures thereof. A particularly preferred diol other than 1,3-propanediol is ethylene glycol, and $C_6$-$C_{10}$ diols can be particularly useful as well.

One preferred PO3G containing comonomers is poly(trimethylene-ethylene ether) glycol such as described in US2004/0030095A1. Preferred poly(trimethylene-ethylene ether) glycols are prepared by acid catalyzed polycondensation of from 50 to about 99 mole % (preferably from about 60 to about 98 mole %, and more preferably from about 70 to about 98 mole %) 1,3-propanediol and up to 50 to about 1 mole % (preferably from about 40 to about 2 mole %, and more preferably from about 30 to about 2 mole %) ethylene glycol.

A preferred PO3G for use in the processes disclosed herein has an Mn (number average molecular weight) of at least about 250, more preferably at least about 1000, and still more preferably at least about 2000. The Mn is preferably less than about 5000, more preferably less than about 4000, and still more preferably less than about 3500. Blends of PO3Gs can also be used. For example, the PO3G can comprise a blend of a higher and a lower molecular weight PO3G, preferably wherein the higher molecular weight PO3G has a number average molecular weight of from about 1000 to about 5000, and the lower molecular weight PO3G has a number average molecular weight of from about 200 to about 950. The Mn of the blended PO3G will preferably still be in the ranges mentioned above.

PO3G preferred for use herein is typically polydisperse, having a polydispersity (i.e. Mw/Mn) of preferably from about 1.0 to about 2.2, more preferably from about 1.2 to about 2.2, and still more preferably from about 1.5 to about 2.1. The polydispersity can be adjusted by using blends of PO3G.

PO3G for use in the present invention preferably has a color value of less than about 100 APHA, and more preferably less than about 50 APHA.

(Meth)Acrylic Esters of Poly(Trimethylene Ether) Glycol

The esterification of the PO3G is carried out by reaction with a (meth)acrylic acid or its equivalent. By "(meth)acrylic acid equivalent" is meant compounds that perform substantially like "(meth)acrylic acid in reaction with polymeric glycols, as would be generally recognized by a person of ordinary skill in the relevant art. Monocarboxylic acid equivalents for the purpose of the present invention include, for example, esters of monocarboxylic acids, and ester-forming derivatives such as acid halides (e.g., acid chlorides) and anhydrides. Mixtures of acrylic acid, methacrylic acid and/or equivalents are also suitable.

The acrylic esters compositions of poly(trimethylene ether) glycol? preferably comprise from about 50 to 100 wt %, more preferably from about 75 to 100 wt %, diester and from 0 to about 100 wt %, more preferably from 50 to about 100 wt %, monoester, based on the total weight of the esters. Preferably the mono- and diesters are esters of (meth)acrylic acid.

Esterification Processes

In one preferred method, the acrylic esters of poly(trimethylene ether) glycol are prepared by polycondensation of hydroxyl groups-containing monomers (monomers containing 2 or more hydroxyl groups) predominantly comprising 1,3-propanediol to form poly(trimethylene ether) glycol in the presence of an acid catalyst, followed by esterification of polytrimethylene ether glycol mixture with the acrylic acid in the presence of a polymerization inhibitor.

For preparation of the esters, the PO3G can be contacted, preferably in the presence of an inert gas, with the (meth) acrylic acid(s) at temperatures ranging from about 25° C. to about 250° C., preferably from about 75° C. to about 150° C. The process can be carried out at atmospheric pressure or under vacuum. During the contacting water is formed and can be removed in the inert gas stream or under vacuum to drive the reaction to completion.

Any ratio of (meth)acrylic acid, or equivalents thereof, to hydroxyl groups can be used. The preferred ratio of acid to hydroxyl groups is from about 3:1 to about 1:2, where the ratio can be adjusted to shift the ratio of mono ester to diester in the product. Generally to favor production of high degree of di(meth)acrylates slightly more than a 1:1 ratio is used. To favor production of monoesters, a 0.5:1 ratio or less of acid to hydroxyl is used.

To facilitate the reaction of PO3G with acrylic acid an esterification catalyst is generally used, preferably a mineral acid catalyst. Examples of acid catalysts include but are not restricted to sulfuric acid, aryl or alkyl sulfonic acid, triflic acid, hydriodic acid, and heterogeneous catalysts such as zeolites, heteropolyacid, amberlyst, dialkyl tin dilaurate, titanium alkoxide and ion exchange resin. Preferred esterification acid catalysts are selected from the group consisting of sulfuric acid, p-toluenesulfonic acid, methanesulfonic acid, triflic acid, dialkyl tin dilaurate, titanium alkoxide, and hydroiodic acid. The particularly preferred acid catalyst are sulfuric acid, triflic acid and ion exchange resins.

The amount of catalyst used can be from about 0.01 wt % to about 10 wt % of the reaction mixture, preferably from 0.1 wt % to about 5 wt %, and more preferably from about 0.2 wt % to about 2 wt %, of the reaction mixture.

To prevent free radical polymerization of acrylic esters of poly(trimethylene ether) glycol, an inhibitor is used, preferably 4-methoxyphenol. Examples of inhibitors include but are not restricted to alkyl phenols, alkoxyphenol, hydroxybezyl alcohol and hydroquinone having structure

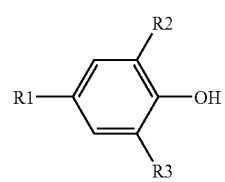

Where R1, R2 and R3 are H, —CH$_3$, —C$_2$H$_5$, —C$_3$H$_7$— C$_4$H$_9$, —OCH$_3$, —OC$_2$H$_5$, —OC$_3$H$_7$—OC$_4$H$_9$, —CH$_2$OH or mixtures thereof. The amount of the inhibitor can be from about 0.001 to 5 wt % of the product. A preferred range is from about 0.01 to 2.0 wt %.

The esterification reaction can be conducted in the presence or absence of a solvent. Examples of solvents include but are not restricted to acetonitrile, cyclohexane, hexane, methylcyclohexane, heptane, octane, tetrahydrofuran, toluene and xylene. A preferred solvent is acetonitrile or toluene. The amount of solvent used can be from about 0 wt % to about 100 wt % of the reaction mixture, preferably from 20 wt % to about 100 wt %, and more preferably from about 50 wt % to about 100 wt %, of the reaction mixture.

A preferred method for esterification comprises polycondensing 1,3-propanediol reactant to polytrimethylene ether glycol using a mineral acid catalyst, then adding (meth) acrylic acid and carrying out the esterification without isolating and purifying the PO3G. In this method, the etherfication or polycondensation of 1,3-propanediol reactant to form polytrimethylene ether glycol is carried out using an acid catalyst as disclosed in U.S. Pat. No. 6,977,291 and U.S. Pat. No. 6,720,459. The etherification reaction may also be carried out using a polycondensation catalyst that contains both an acid and a base as described in JP2004-182974A. The polycondensation or etherification reaction is continued until desired molecular weight is reached, followed by the addition of solvent, calculated amount of (meth)acrylic acid and an inhibitor to the reaction mixture. The mixture is refluxed where about 30 to 70% esterification takes place. The reaction is continued further while the water byproduct and solvent are removed while further esterification is in progress. In this preferred esterification method the acid catalyst used for polycondensation of diol is also used for esterification. If necessary additional esterification catalyst can be added at the esterification stage.

In an alternative procedure, the esterification reaction can be carried out by reacting neat PO3G with (meth)acrylic acid or (meth)acrylic acid equivalent in the presence of an esterification catalyst followed by heating and removal of byproduct.

In an another alternative procedure, the esterification reaction can be carried out by reacting neat PO3G with (meth) acrylic acid chloride in the presence of an organic base such trialkylamine at low temperatures followed by heating.

The ester produced in the esterification reaction may contain diester, monoester, or a combination of diester and monoester, and small amounts of acid catalyst, unreacted (meth)acrylic acid and diol depending on the reaction conditions. If desired, this product mixture is further processed to remove acid catalyst, unreacted carboxylic acid, and diol by the known conventional techniques such as water washings, base neutralization, filtration and/or distillation. Unreacted diol and acid catalyst can, for example, be removed by washing with deionized water. Unreacted carboxylic acid also can be removed, for example, by washing with deionized water or aqueous base solutions.

Proton NMR can be used to identify the product of the esterification reaction, quantify the esterification and determine the number average molecular weight.

The obtained polytrimethylene ether glycol acrylates have the following structural formula (I):

$$CH_2=CR_1-C(O)-O-Q-OR_2 \quad (I)$$

wherein Q represents the residue of a polytrimethylene ether glycol after abstraction of the hydroxyl groups, $R_1$ is H or $CH_3$, and each of $R_2$ is H or $CH_2=CR_1-C(O)$. Q has Mn within the range of from about 134 to about 5000.

Each acrylic ester of the polytrimethylene ether glycol produced by the above disclosed process can further react with itself to make homopolymers, or can be reacted with another acrylic or vinyl monomer to create a broad range of copolymers with different tailored properties. The following acrylic ester monomers are among those useful for copolymerization: methyl acrylate, methyl methacrylate, ethyl acrylate, propyl acrylate, isopropyl acrylate, n-butyl acrylate, sec-butyl acrylate, isobutyl acrylate, tert-butyl acrylate, hexyl acrylate, heptyl acrylate, 2-heptyl acrylate, 2-ethylhexyl acrylate, 2-ethylbutyl acrylate, dodecyl acrylate, hexadecyl acrylate, isobornyl acrylate, and cyclohexyl acrylate. If it is desired two or more monomers can be used for the copolymerization. Beside the acrylic ester monomers, the acrylic esters of the polytrimethylene ether glycol disclosed herein can be reacted with other type of monomers such as: acrylonitrile, butadiene, styrene, vinyl chloride, vinylidene chloride, and vinyl acetate.

Free radical initiators such as azo compounds (e.g. 2,2'-azobisizobutironitrile), peroxides (e.g. hydrogen peroxide, benzoyl peroxide), or hydroperoxides can be used to initiate of the polymerization of acrylic ester monomers. Photochemical and radiation-initiated polymerization are also possible. The desired homo- and copolymer compositions can be obtained by bulk, solution, emulsion or suspension polymerization. In case of the copolymers the acrylic esters of the polytrimethylene ether glycol content can vary from 1% to 99% and the other co-monomer content can vary from 1% to 99%, more preferable from 1% to 50%, and most preferable from 1% to 25%.

Materials made by the processes disclosed herein find use in a wide range of applications, including use as free radical crosslinkers, in polymer dispersions, in paints, coatings for wood, paper and plastics; inks; adhesives; lithography; and printed circuits. Many of the systems containing products of the processes disclosed herein are radiation curable, i.e., the materials are crosslinked when exposed to a source of radiation. Also, the processes provide renewably-sourced polymers, which can find use as functional comonomers for flexible plastics, crosslinking agent and coagents, and the like. These products exhibit higher flexibility, higher resistance to reverse impact, and lower shrinkage than similar products that are not based on poly(trimethylene ether) glycol diacrylate.

Acrylic emulsion polymers can be used in animal leather production providing uniformity, break improvement, better durability and surface resistance. The obtained polymers can be useful items in the ceramic industry and can work as binders, deflocculants and additives. These polymers have a variety of uses in textile applications, including textile bonding and laminating, flocking, backcoating and pigment printing applications. Acrylics also used as binders for fiberfill and nonwoven fabrics. Acrylics are often used in automotive applications as backing of carseats and also as backing for furniture upholstery. In cosmetics and personal care formulations acrylics are broadly used as thickening agents.

The poly(trimethylene ether) glycol diacrylates formed from the processes disclosed herein can overcome some of the difficulties associated with similar materials. For example, poly(ethylene) glycol diacrylate is a linear, semicrystalline polymer having primary reactive difunctionality. Likewise, it is possible to make difunctional acrylates from poly(propylene) and poly(tetramethylene) glycols; however, these polymers generally undergo degradation during synthesis. The diacrylates formed from the processes disclosed herein overcome these difficulties by allowing the production of higher molecular weight diacrylates as well as materials which do not undergo degradation during synthesis.

EXAMPLES

The present invention is further defined in the following examples. These examples, while indicating preferred embodiments of the invention, are presented by way of illustration only. From the above discussion and these examples, one skilled in the art can ascertain the essential characteristics of this invention, and without departing from the spirit and scope thereof, can make various changes and modifications of the invention to adapt it to various usages and conditions.

All parts, percentages, etc., are by weight unless otherwise indicated.

Susterra® propanediol and Cerenol™ polyols are commercially available from DuPont Tate &Lyle Bioproducts, LLC (Loudon, Tenn.) and DuPont de Nemours Co. Inc., (Wilmington, Del.) respectively.

The number average molecular weights (Mn) were determined by end-group analysis using NMR spectroscopic method. This method was also used to identify and quantify the percent esterification and un-reacted acrylic acid in the polymer.

1H NMR spectra were recorded on Bruker DRX 500 using XWINNMR version 3.5 software. Data was acquired using a 90 degree pulse (p1) and a 30 second recycle delay (d1). Samples were dissolved in deuterated chloroform and non-deuterated chloroform was used as internal standard.

Example 1

Synthesis of Acrylic Ester of Poly(Trimethylene Ether) Glycol Starting from Susterra® Propanediol Susterra® propanediol (3.04 kg), 27.58 g of concentrated sulfuric acid (EMD, 95%) and 14.06 g $Na_2CO_3$ solution (1.46 g of $Na_2CO_3$ dissolved in 12.6 g of water) were charged into a 5 L flask fitted with a stirrer, a condenser and an inlet for nitrogen. The mixture was heated to 166° C. while stirring for 8 hours. A total of 550 mL of distillate was collected during this period. The obtained poly(trimethylene ether) glycol product was analyzed by NMR and has number average molecular weight 278.

A portion of the above product (61.2 g), 60 g acetonitrile, 0.3 g methoxyphenol and 31.1 g of acrylic acid were taken in a 250 mL three neck round-bottom flask and this mixture was refluxed for 3 hours. After three hours, a distillation head was attached to the flask and the solvent was distilled out from the reaction mixture at 85° C. The temperature was slowly raised to 115° C. and the reaction was allowed to continue for 90 minutes at 115° C. The reaction mixture was allowed to cool to room temperature and then diluted with 100 mL of deionized (DI) water. To purify the aqueous mixture, it was mixed thoroughly and transferred to separating funnel. The organic product was collected and dried using rotary evaporator at 35° C. The acrylic ester product, was stabilized by 200 ppm of 2,6-bis(1,1-dimethylethyl)-4-methylphenol (BHT) and the product was analyzed using proton NMR as shown in Table 1.

Example 2

Synthesis of Acrylic Ester of Poly(Trimethylene Ether) Glycol Starting from Cerenol™ H1400 and Acrylic Acid 91 g Cerenol™ H1400, 90 g of acetonitrile, 0.1 g 4-methoxyphenol, and 9.5 g acrylic acid were taken in 250 mL three neck round-bottom flask. The ingredients were thoroughly mixed, then 0.46 g of $H_2SO_4$ (95 wt %) was added and the reaction mixture was heated and refluxed for 5 hours. The solvent was removed and then the reaction temperature was slowly raised to 115° C. and the reaction was allowed to continue for 3 hours at 115° C. The product was further purified as described in example 1. 200 ppm of BHT was added to the final product. The acrylic ester product was analyzed before and after purification using proton NMR as shown in Table 1.

Example 3

Synthesis of Acrylic Ester of Poly(Trimethylene Ether) Glycol Starting from Cerenol™ H1400 and Acrylic Acid 91 g Cerenol™ H1400, 90 g of acetonitrile, 0.1 g 4-methoxyphenol and 9.5 g of acrylic acid were mixed in 250 mL three neck RB flask. To this mixture, 0.46 g of $H_2SO_4$ (95 wt %) was added and the reaction mixture was heated to 83° C. (±1°). The reaction was carried out for 5 hours under reflux conditions. After five hours, distillation head was attached and the solvent was removed by distillation at 85° C. After solvent was distilled out the reaction temperature was slowly raised to 125° C. and the reaction was allowed to continue for 2 hours at 125° C. 200 ppm of BHT was added to the final product.

The resulting acrylic ester product was analyzed using proton NMR as shown in Table 1.

Example 4

Synthesis of Acrylic Ester of Poly(Trimethylene Ether) Glycol Starting from Cerenol™ H1740 and Acryloyl Chloride 49.8 g of poly(trimethylene ether) glycol (Mn=1740) and 6.9 g of triethylamine (Aldrich, 99.5%) were taken into a three neck glass reactor. The mixture was then cooled to 8° C. using ice bath. Dry nitrogen gas was passed over the reaction mixture for an hour to remove air and moisture. 6.3 g of acryloyl chloride (Aldrich, 98%) was added slowly while the mixture was thoroughly agitated and the temperature was kept below 12° C. After the addition was completed, ice from the ice bath was replaced with water to increase the reaction temperature in a controlled way and avoid any sudden rise in temperature. After bringing the reaction to 28° C., the reaction mixture was stirred for 30 minutes. The reaction temperature was slowly raised to 60° C. and maintained at that temperature for 6 hours. The reaction mixture was cooled to about 35° C. and then 50 mL of 5% KOH solution, 100 mL of dichloromethane and 50 mL water were added. The mixture was agitated thoroughly for 30 minutes and transferred into a separating funnel. The resulting product was allowed to settle overnight. The organic part of the mixture was isolated and 500 ppm of 4-methoxy phenol was added. The solvent was removed using rotary evaporator under reduced pressure (300 to 500 mTorr) at 30° C. 200 ppm of BHT was added to the final product. The obtained product was analyzed using NMR as shown in Table 1.

TABLE 1

| Example | Crude/Purified | Product Mn | Esterification (mole %) | Un-reacted acrylic acid, wt % |
|---------|----------------|------------|-------------------------|-------------------------------|
| 1 | Crude | 376 | 85.4 | 1.2 |
|   | Purified | 390 | 88.9 | 0.3 |
| 2 | Crude | 1484 | 71.7 | 4.1 |
|   | Purified | 1508 | 71.7 | 0.3 |
| 3 | Crude | 1509 | 75.4 | 2 |
| 4 | Purified | 1844 | 100 | 0 |

What is claimed is:

1. A process for making a (meth)acrylic acid ester of a polytrimethylene ether glycol comprising:
   a) polycondensation of hydroxyl groups-containing monomers predominantly comprising 1,3-propanediol obtained biochemically from a renewable source in the presence of acid catalyst at temperatures between 100 to 250° C. to form a poly(trimethylene ether) glycol,
   b) esterifying the obtained poly(trimethylene ether) glycol with an acrylic compound in the presence of a polymerization inhibitor(s) and optionally a solvent at temperatures between 25 to 250° C.,
   wherein the (meth)acrylic acid ester of a polytrimethylene ether glycol is a mixture of mono and diesters of poly(trimethylene ether) glycol.

2. A process for making a (meth)acrylic acid ester of a polytrimethylene ether glycol comprising: reacting poly(trimethylene ether) glycol having a number average molecular weight from 134 to 5000 with (meth)acrylic acid in the presence of an esterification catalyst, a polymerization inhibitor and optionally a solvent at temperatures between 25 to 250° C., wherein the (meth)acrylic acid ester of a polytrimethylene ether glycol is a mixture of mono and diesters of polytrimethylene ether) glycol.

3. The process of claim 1, further comprising isolating poly(trimethylene ether) glycol acrylate.

4. The process of claim 2, wherein the poly(trimethylene ether) glycol is derived from a renewable source.

5. The process of claim 1, wherein the catalyst is sulfuric acid, aryl or alkyl sulfonic acid, triflic acid, or ion exchange resins.

6. The process of claim 2, wherein the esterification catalyst is dialkyl tin dilaurate, titanium alkoxide, mineral acid or combination thereof.

7. The process of claim 1, wherein the polymerization inhibitor is selected from the group consisting of alkoxyphenol, alkyl phenols, alkoxyphenol, hydroxybenzyl alcohol, and compounds having a structure

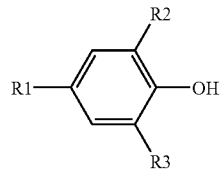

wherein R1, R2 and R3 are independently selected from the group consisting of: H, —$CH_3$, —$C_2H_5$, —$C_3H_7$—$C_4H_9$, —$OCH_3$, —$OC_2H_5$, —$OC_3H_7$, —$OC_4H_9$, and —$CH_2OH$.

* * * * *